(12) United States Patent
Kang et al.

(10) Patent No.: US 8,137,849 B2
(45) Date of Patent: Mar. 20, 2012

(54) PHOSPHATE-BASED ACRYLATE CROSSLINKING AGENT FOR POLYMER ELECTROLYTE AND A COMPOSITION CONTAINING THE SAME

(75) Inventors: Yongku Kang, Daejeon (KR); Changjin Lee, Daejeon (KR); Jun Kyoung Lee, Daejeon (KR); Joung In Lee, Chungcheongnam-do (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 509 days.

(21) Appl. No.: 12/375,057

(22) PCT Filed: Jul. 26, 2007

(86) PCT No.: PCT/KR2007/003600
§ 371 (c)(1),
(2), (4) Date: Jan. 26, 2009

(87) PCT Pub. No.: WO2008/013417
PCT Pub. Date: Jan. 31, 2008

(65) Prior Publication Data
US 2010/0003604 A1 Jan. 7, 2010

(30) Foreign Application Priority Data
Jul. 26, 2006 (KR) .................. 10-2006-0070441

(51) Int. Cl.
*H01M 6/16* (2006.01)

(52) U.S. Cl. ........ 429/341; 429/345; 429/200; 429/330; 429/337; 429/329; 429/339; 252/62.2

(58) Field of Classification Search ............ 429/341, 429/345, 200, 330, 337, 329, 339; 252/62.2; 558/180
See application file for complete search history.

(56) References Cited

FOREIGN PATENT DOCUMENTS
| WO | WO 00/29456 | * | 5/2000 |
| WO | WO 00/50527 | * | 8/2000 |
| WO | WO 2007/080812 | * | 7/2007 |

* cited by examiner

*Primary Examiner* — Laura Weiner
(74) *Attorney, Agent, or Firm* — Frommer Lawrence & Haug LLP; Ronald R Santucci

(57) ABSTRACT

The present invention relates to a phosphate-based acrylate crosslinking agent for polymer electrolyte and a polymer electrolyte composition comprising the phosphate-based acrylate crosslinking agent, and in particular to a phosphate-based acrylate crosslinking agent where a phosphate-based compound is introduced with a polyalkylene oxide group and an acrylate group and a polymer electrolyte composition comprising the phosphate-based acrylate crosslinking agent. The polymer electrolyte composition can be applied to electrolyte thin film and polymer electrolyte of small and large capacity lithium-polymer secondary battery due to its superior ionic conductivity and electrochemical and thermal stability, where the physical properties of electrolyte composition may be controlled by means of the length of polyalkylene oxide of the crosslinking agent.

12 Claims, 2 Drawing Sheets

[Figure 1]
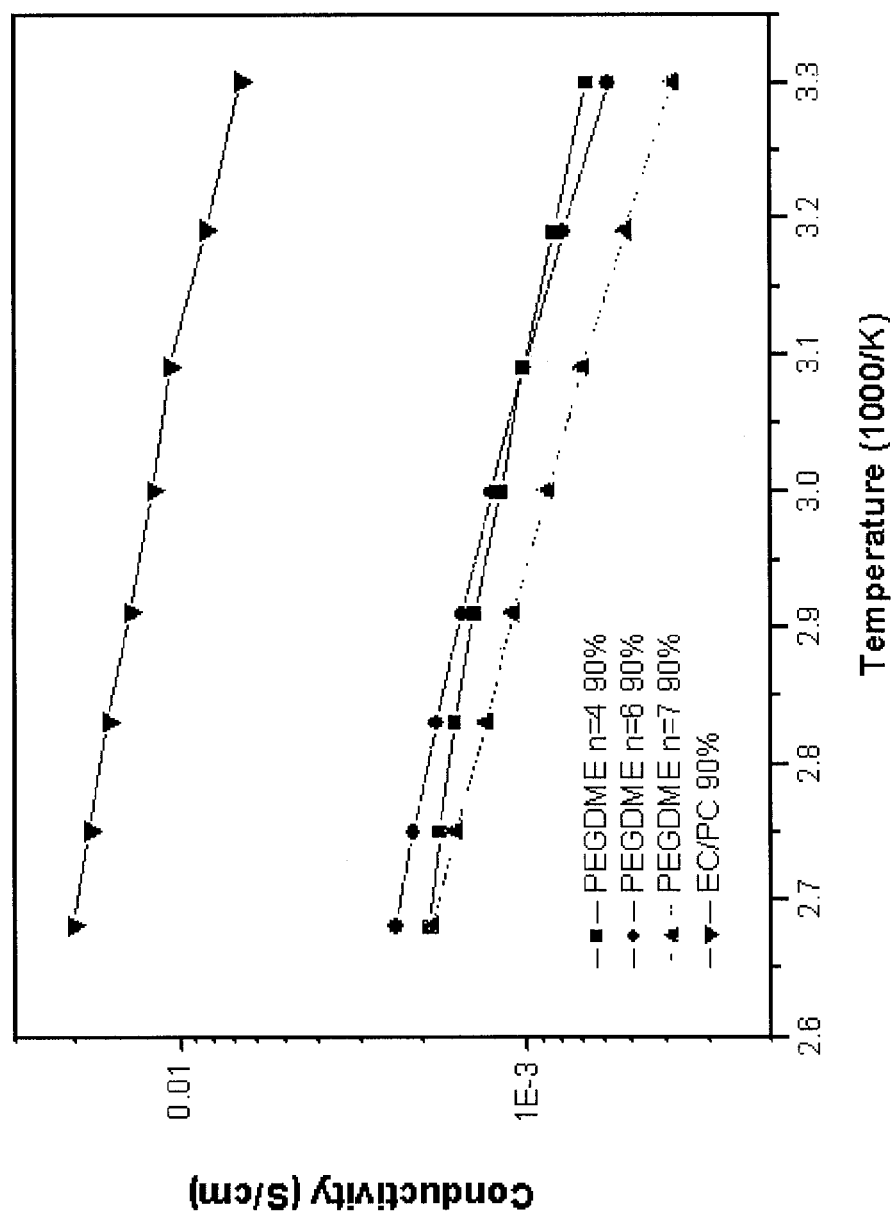

[Figure 2]
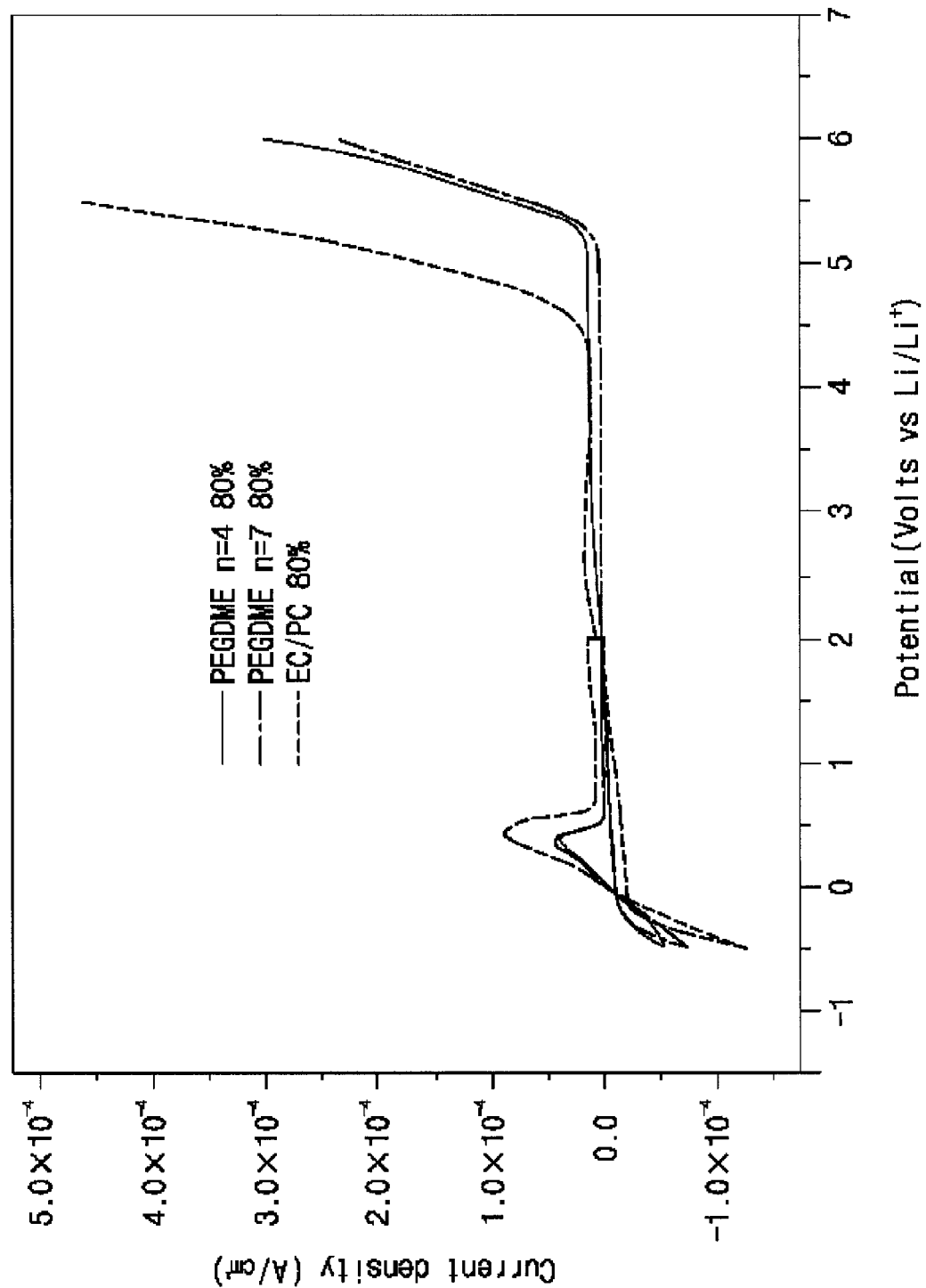

PHOSPHATE-BASED ACRYLATE CROSSLINKING AGENT FOR POLYMER ELECTROLYTE AND A COMPOSITION CONTAINING THE SAME

This application is a 371 of PCT/KR2007/003600 filed on Jul. 26, 2007, published on Jan. 31, 2008 under publication number WO 2008/013417 A1 which claims priority benefits from South Korean Patent Application Number 10-2006-0070441 filed Jul. 26, 2006, the disclosure of which is incorporated herein by reference.

TECHNICAL FIELD

The present invention relates to a phosphate-based acrylate crosslinking agent for polymer electrolyte and a polymer electrolyte composition comprising the phosphate-based acrylate crosslinking agent, and in particular to a polymer electrolyte composition comprising the crosslinking agent, and in particular to a phosphate-based acrylate crosslinking agent where a phosphate-based compound is introduced with a polyalkylene oxide group and an acrylate group and a polymer electrolyte composition comprising the phosphate-based acrylate crosslinking agent. The polymer electrolyte composition is applicable to electrolyte thin film and polymer electrolyte of small and large capacity lithium-polymer secondary battery due to its superior ionic conductivity and electrochemical and thermal stability, where the physical properties of electrolyte composition may be controlled by means of the chaining the chain length of polyalkylene oxide of the crosslinking agent.

BACKGROUND ART

Because the conventional electrochemical device comprising liquid electrolyte has stability problems such as electrolyte leakage and explosion, an electrochemical device using polymer electrolyte has been developed. For example, lithium-polymer battery comprising polymer electrolyte has many advantages over to the conventional ones in that it is superior in stability, more economical due to its improved charge-discharge efficiency, can be designed into various shapes and be manufactured in the form of a thin-film, thus enabling to reduce the battery size.

In particular, polyalkylene oxide (PAO)-based solid polymer, which has been widely used as polymer electrolytes, and gel-type polymer electrolytes, which comprise organic liquid electrolytes in the polymer, have been of great concern as polymer electrolytes in the field of lithium secondary battery. Polyalkylene oxide of low molecular weight or an organic solvent has been added as a plasticizer to increase the conductivity of polymer electrolyte. However, it has drawbacks that the physical properties of polymer electrolytes may be deteriorated or the stable gel electrolyte cannot be prepared when its plasticizer content is increased.

U.S. Pat. No. 4,830,939 and J. Electrochemm. Soc., 145, 1521 (1998) disclose a process of preparing a crosslinked polymer electrolyte by means of UV or electronic beam irradiation by using a mixture of an ion conductive liquid comprising a polyalkylene glycol compound having a chemically crosslinkable group and an electrolyte salt.

U.S. Pat. Nos. 5,830,600, 6,511,772 and 6,746,794 disclose the use of a fire-retardant additive for a non-aqueous electrolyte solvent to improve the thermal stability of a lithium secondary battery. A phosphate-based compound was used as the fire-retardant additive.

DISCLOSURE

Technical Solution

The present inventors have conducted extensive researches to improve the ionic conductivity and thermal stability of the polymer electrolyte composition comprising polyalkylene glycol. As a result, they have finally succeeded in developing a novel crosslinking agent where a polyalkylene oxide group and a photo- or thermal crosslinkable acrylate group are introduced to a phosphate-based compound with fire-retardancy, and a polymer electrolyte composition comprising the crosslinking agent that is superior in ionic conductivity, electrochemical and thermal stability.

Therefore, the present invention aims to provide a phosphate-based acrylate crosslinking agent for polymer electrolyte, which comprises a polyalkylene oxide group and an acrylate group.

The present invention also aims to provide a polymer electrolyte composition comprising the phosphate-based acrylate crosslinking agent for polymer electrolyte.

DESCRIPTION OF DRAWINGS

FIG. 1 shows the temperature dependency of ionic conductivity of solid polymer electrolytes prepared using various plasticizers of the present invention.

FIG. 2 shows the electrochemical stability of solid polymer electrolytes prepared using various plasticizers of the present invention. The electrochemical stability was measured by means of the linear sweep voltammetry.

MODE FOR INVENTION

The present invention relates to a phosphate-based acrylate crosslinking agent for polymer electrolyte of Formula 1:

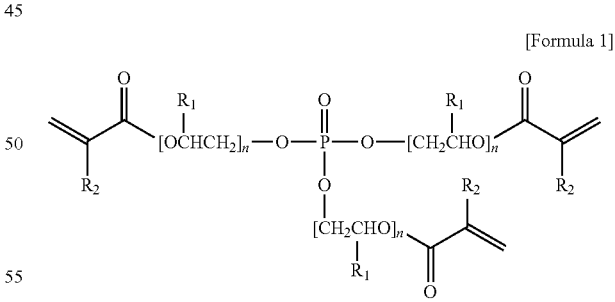

[Formula 1]

wherein $R_1$ and $R_2$ are respectively a hydrogen atom or a methyl group; and n is an integer of 1-20.

The present invention also relates to a solid polymer electrolyte composition, which comprises 0.1-95 wt % of a phosphate-based acrylate crosslinking agent of Formula 1; 0.1-98 wt % of one or more of a plasticizer selected from the group consisting of polyalkylene glycol dialkyl ether of Formula 2 and a polar aprotic solvent; 3-40 wt % of a lithium salt; and 0.1-5 wt % of an initiator:

[Formula 2]

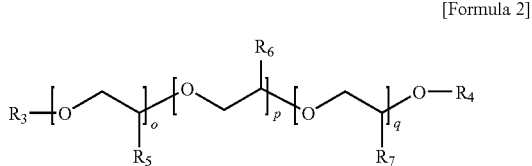

wherein $R_3$ and $R_4$ are respectively a $C_1$-$C_{10}$ linear or branched alkyl group; $R_5$, $R_6$ and $R_7$ are respectively a hydrogen atom or a methyl group; and o, p and q are respectively an integer of 0-20 except when all of o, p and q are zero at the same time.

Hereunder is provided a detailed description of the present invention.

The present invention relates to a photo- and thermal-crosslinkable phosphate-based acrylate crosslinking agent where a polyalkylene oxide group and an acrylate group are introduced to a phosphate-based compound, and a polymer electrolyte composition comprising the phosphate-based acrylate crosslinking agent, a specific plasticizer, lithium salt and photo or thermal initiator, having superior ionic conductivity, electrochemical and thermal stability at room temperature due to improved compatibility.

Although "Polymer Degradation Stability 84 (2004) 525-532" discloses the phosphate-based acrylate crosslinking agent, this disclosure is for UV crosslinking agent for a coating purpose, which is different from the use as a crosslinking agent for polymer electrolyte in the present invention.

The process of preparing a phosphate-based acrylate of Formula 1 is provided in Scheme 1 below,

[Scheme 1]

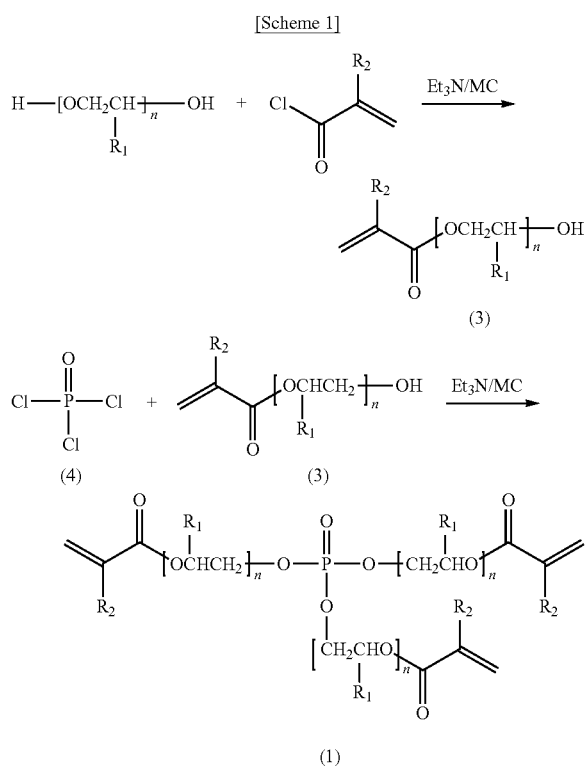

wherein $R_1$, $R_2$ and n are same as defined above.

As shown in Scheme 1, tris(acryloyl polyethylene glycol) phosphate (POA) of Formula 1 is synthesized by reacting phosphorous oxytrichloride ($POCl_3$) of Formula 4 with polyethylene glycol mono acrylate (HOA) of Formula 3. The polyethylene glycol mono acrylate (HOA) of Formula 3 may be prepared under a conventionally used condition, preferably at 0° C. for 12 hours under nitrogen atmosphere.

The phosphate-based acrylate compound of Formula 1 may be used as a crosslinking agent in various fields, for example, to improve electrochemical or thermal stability by inhibiting the combustion or explosion caused by an organic solvent. In particular, the phosphate-based compound is known as a fire retardant, and may improve the stability of a lithium battery when applied to a gel-type electrolyte comprising a volatile organic solvent.

Considering the aforementioned properties of a phosphate-based acrylate compound herein, the present invention aims to provide a solid polymer electrolyte composition comprising a phosphate-based acrylate compound as a crosslinking agent. A polymer electrolyte composition herein may be applied without limitation, for example, to an electrolyte thin film or a polymer electrolyte of small or high capacity lithium-polymer secondary battery.

A solid polymer electrolyte composition herein comprises 0.1-95 wt % of a phosphate-based acrylate crosslinking agent of Formula 1; 0.1-98 wt % of one or more of a plasticizer selected from the group consisting of polyalkylene glycol dialkyl ether of Formula 2 and a polar aprotic solvent; 3-40 wt % of a lithium salt; and 0.1-5 wt % of an initiator:

[Formula 2]

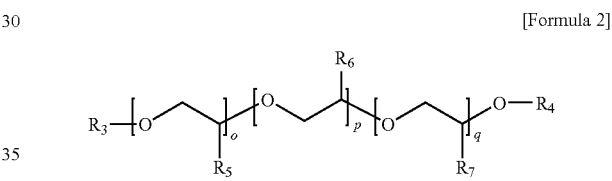

wherein $R_3$ and $R_4$ are respectively a $C_1$-$C_{10}$ linear or branched alkyl group; $R_5$, $R_6$ and $R_7$ are respectively a hydrogen atom or a methyl group; and o, p and q are respectively an integer of 0-20 except when all of o, p and q are zero at the same time.

A phosphate-based acrylate compound of Formula 1 is used as a crosslinking agent. The polyalkylene oxide group introduced into the phosphate-based acrylate compound improves the compatibility with a plasticizer to be added for increasing ionic conductivity of electrolyte, whereas the acrylate group to be added as well into the phosphate-based acrylate compound enables to establish the 3D network structure of polymer electrolyte.

The crosslinking agent is contained in a polymer electrolyte composition in the amount of 0.1-95 wt %, preferably 0.5-80 wt %, more preferably 0.5-60 wt %. When the amount is less than 0.1 wt %, the role as a crosslinking agent may not be sufficient and mechanical property may be also lowered. When the amount exceeds 95 wt %, ionic conductivity may be decreased.

The plasticizer of Formula 2 is used to improve the ionic conductivity by improving the dissociation of a lithium salt and the conductivity of the lithium ion, and may be selected among polyalkylene glycol dialkyl ether of Formula 2, a polar aprotic solvent and a mixture thereof.

Examples of the polyalkylene glycol dialkyl ether of Formula 2 include polyethylene glycol dimethyl ether, polyethylene glycol diethyl ether, polyethylene glycol dipropyl ether, polyethylene glycol dibutyl ether, polyethylene glycol diglycidyl ether, polypropylene glycol dimethyl ether, polypropylene glycol diglycidyl ether, a copolymer of polypropylene glycol having dibutyl ether end/polyethylene glycol and a block copolymer of polyethylene glycol having dibutyl ether end/polypropylene glycol/polyethylene glycol.

The polar aprotic solvent may be selected among alkylene carbonate-based, alkyltetrahydrofuran-based, dioxirane-based, lactone-based and acetonitrile-based solvents. The examples include ethylene carbonate, propylene carbonate, butylene carbonate, dimethyl carbonate, tetrahydrofuran, 2-methyltetrahydrofuran, 1,3-dioxirane, 4,4-dimethyl-1,3-dioxirane, γ-butylolactone and acetonitrile.

The plasticizer is preferably contained in a polymer electrolyte composition in the amount of 0.1-98 wt %, preferably 0.1-90 wt %. In general, the increase in plasticizer content in a polymer electrolyte is directly proportional to the increase in ionic conductivity of a polymer electrolyte. However, if the plasticizer content exceeds 98 wt % it greatly reduces mechanical property of a polymer electrolyte, and thus cannot be used as a thin film for manufacturing a battery. Therefore, a thin film with a thickness of 100 μm or less can be manufactured only when the plasticizer content is maintained within the aforementioned range.

Further, any conventional lithium salt used for the manufacture of a polymer electrolyte may be used in the present invention. Examples of the lithium salt are $LiClO_4$, $LiCF_3SO_3$, $LiBF_4$, $LiPF_6$, $LiAsF_6$ and $Li(CF_3SO_2)_2N$.

The lithium salt is contained in a polymer electrolyte composition in the amount of 3-40 wt %, preferably 5-25 wt %. However, the amount may be adjusted if necessary. When the amount is less than 3 wt %, the concentration of a lithium ion is not sufficient to be used as an electrolyte. Meanwhile, if it exceeds 40 wt % it may be difficult to dissolve a lithium salt and decrease ionic conductivity.

Conventional thermal- or photo-initiators may be used as an initiator in the present invention. Examples of the photo initiator include ethylbenzoyn ether, isopropylbenzoyn ether, α-methylbenzoyn ethyl ether, benzoyn phenyl ether, α-acyloxime ester, α,α-diethoxy acetophenone, 1,1-dichloroacetophenone, 2-hydroxy-2-methyl-1-phenylpropane-1-one [Darocure 1173 of Ciba Geigy], 1-hydroxycyclohexyl phenyl ketone [Irgacure 184, Darocure 1116, Irgacure 907 of Ciba Geigy], anthraquinone, 2-ethyl anthraquinone, 2-chloro anthraquinone, thioxanthone, isopropyl thioxanthone, chlorothioxanthone, benzophenone, p-chlorobenzophenone, benzyl benzoate, benzoyl benzoate and Michler's ketone. Examples of the thermal initiator include azoisobutyronitrile-based and peroxide-based initiators.

The initiator may be contained in a polymer electrolyte composition in the amount of 0.1-5 wt %. When the amount is less than 0.1 wt %, the initiation for crosslinking reaction may not be sufficient. When the amount exceeds 5 wt %, the non-reacted initiator remaining after the crosslinking may deteriorate the performance of a battery to be manufactured thereof. The amount of the initiator may be appropriately determined considering the contents of other components.

A solid polymer electrolyte composition according to the present invention may be used for a thin film of electrolyte and a polymer electrolyte of lithium-polymer secondary battery.

Hereunder is provided description of the preparation of electrolyte thin film prepared by using a solid polymer electrolyte composition only for illustration purpose. The present invention is not limited to the embodiments described herein below.

First, a plasticizer and a lithium salt are added in a container in an appropriate ratio, mixed by stirring to become a solution, and then a crosslinking agent is added thereto. An initiator is added to this mixture and mixed, thereby providing a composition for solid polymer electrolyte. This composition is coated on a glass, polyethylene-based film or commercial Mylar film or on a battery electrode, crosslinked by the irradiation of electronic beams, UV or gamma ray or thermal treatment.

As another way to obtain a film with a predetermined thickness, the composition is coated on the support. Spacers for controlling the thickness are fixed on both ends of the support, and covered with another support. A thin film for solid polymer electrolyte is prepared by means of the aforementioned irradiation or thermal treatment.

Hereunder is provided a detailed description of a process for preparing a polymer electrolyte for manufacturing a lithium-polymer secondary battery, i.e. another embodiment for applying the solid polymer electrolyte composition of the present invention.

A lithium-polymer secondary battery consists of an anode, an electrolyte and a cathode. Lithium metal oxide such as $LiCoO_2$ and $LiNiO_2$ is used as an anode. A carbon-based material such as graphites (e.g., MCMB and MPCF) and cokes or lithium metals is used as a cathode. A crosslinking agent herein, a plasticizer, a lithium salt and an initiator are mixed to provide an electrolyte solution. A film with a predetermined thickness is prepared by using the solution. A polymer electrolyte is prepared by photo- or thermal-crosslinking for a predetermined period of time.

A lithium-polymer secondary battery may be prepared according to any conventional process.

As described above, by using the novel phosphate-based acrylate compound of the present invention as a crosslinking agent of a solid polymer electrolyte composition, properties of electrolytes such as mechanical strength, ionic conductivity and thermal stability can be greatly improved due to the aforementioned chemical or structural property.

The present invention is described more specifically by the following Examples. Examples herein are meant only to illustrate the present invention, but they should not be construed as limiting the scope of the claimed invention.

PREPARATION EXAMPLE

Preparation of Polyethylene Glycol Monoacrylate (HOA)

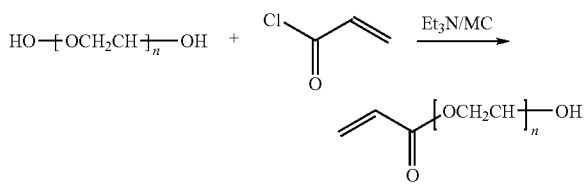

Preparation Example 1

Hydroxy Ethoxy Acrylate

A commercially available hydroxy ethyl acrylate (Aldrich) was used for hydroxy ethoxy acrylate (HOA, n=1).

Preparation Example 2

Hydroxy tri(ethoxy) acrylate

Triethylene glycol (20 g, 0.133 mol, n=3) and triethyl amine (13.5 g, 0.133 mol) were dissolved in 200 mL of dichloromethane in a 3-neck round flask, followed by drop-wise addition of the solution of acryloyl chloride (12 g, 0.133 mol in 100 mL of dichloromethane) with stirring at 0° C. After about 12-hour reaction, precipitates were removed and products were obtained by evaporation under reduced pressure. White viscous liquid products were dissolved in dichloromethane, and extracted several times with water. The dichloromethane layer was separated, dried with $MgSO_4$ and evaporated under reduced pressure. The crude product was purified by using a silica column chromatography, thereby providing about 12 g of hydroxy tri(ethoxy)acrylate (HOA, n=3) (yield 45%)

$^1$H-NMR (300 MHz, $CDCl_3$): 3.05-3.15 (s, 1H), 3.52-3.67 (m, 10H), 4.3-4.4 (m, 2H), 5.7-5.85 (d, 1H), 6.0-6.2 (m, 1H), 6.3-6.45 (d, 1H).

Preparation Example 3

Hydroxy penta(ethoxy) acrylate

Experiment was conducted same as in Preparation Example 2 except that 32 g of pentaethylene glycol (n=5), 8.5 g of triethylamine and 7.6 g of acryloyl chloride were reacted, thereby providing 16.7 g of hydroxy penta(ethoxy) acrylate (HOA, n=5) (yield 43%).

$^1$H-NMR (300 MHz, $CDCl_3$): 3.05-3.15 (s, 1H), 3.52-3.67 (m, 18H), 4.3-4.4 (m, 2H), 5.7-5.85 (d, 1H), 6.0-6.2 (m, 1H), 6.3-6.45 (d, 1H).

Preparation Example 4

Polyethylene Glycol Monoacrylate

Experiment was conducted same as in Preparation Example 2 except that 135 g of polyethylene glycol (n=13.2, molecular weight 1,000), 8.5 g of triethylamine and 7.6 g of acryloyl chloride were reacted, thereby providing 54.6 g of polyethylene glycol mono acrylate (HOA, n=13.2) (yield 39%).

$^1$H-NMR (300 MHz, $CDCl_3$): 3.05-3.15 (s, 1H), 3.52-3.67 (m, 51H), 4.3-4.4 (m, 2H), 5.7-5.85 (d, 1H), 6.0-6.2 (m, 1H), 6.3-6.45 (d, 1H).

EXAMPLE

Preparation of Phosphate-Based Acrylate
(Formula 1)

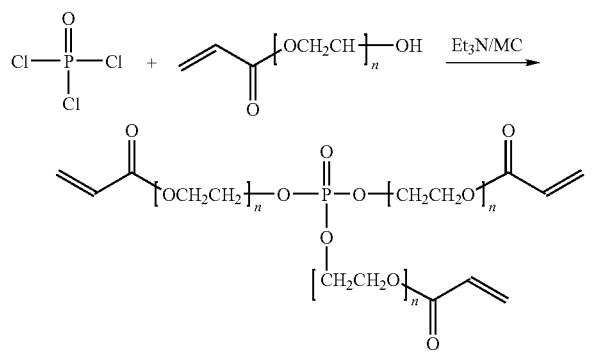

Example 1

Tris(acryloylethoxy) phosphate

Hydroxy ethoxy acrylate (12 g, 0.1 mol) and triethylamine (10.5 g, 0.1 mol) were dissolved in 100 mL of dichloromethane in a 3-neck round flask, followed by drop-wise addition of the solution of phosphorous oxytrichloride (5 g, 0.0326 mol in 80 mL of dichloromethane) with stirring at 0° C. After about 12-hour reaction, precipitates were removed and products were obtained by evaporation under reduced pressure. White viscous liquid products were dissolved in dichloromethane, and extracted several times with water. The dichloromethane layer was separated, dried with $MgSO_4$ and evaporated under reduced pressure. The crude product was purified by using a silica column chromatography, thereby providing about 12 g of hydroxy tris(acryloylethoxy) phosphate (POA, n=1) (yield 45%).

$^1$H-NMR (300 MHz, $CDCl_3$): 4.2-4.45 (m, 12H), 5.7-5.85 (d, 3H), 6.0-6.2 (m, 3H), 6.3-6.45 (d, 3H).

Example 2

Tris(acryloyltriethoxy) phosphate

Experiment was conducted same as in Example 1 except that 5.2 g of hydroxyl tri(ethoxy) acrylate prepared in Preparation Example 2, 2.58 g of triethylamine and 1.18 g of phosphorous oxytrichloride were reacted, thereby providing 2.5 g of tris(acryloyltriethoxy) phosphate (POA, n=3) (yield 50%).

$^1$H-NMR (300 MHz, $CDCl_3$): 4.2-4.45 (m, 36H), 5.7-5.85 (d, 3H), 6.0-6.2 (m, 3H), 6.3-6.45 (d, 3H).

Example 3

Tris(acryloylpentaethoxy) phosphate

Experiment was conducted same as in Example 1 except that 5 g of hydroxy penta(ethoxy) acrylate prepared in Preparation Example 3, 1.73 g of triethylamine and 0.8 g of phosphorous oxytrichloride were reacted, thereby providing 2 g of tris(acryloyltriethoxy) phosphate (POA, n=5) (yield 45%).

$^1$H-NMR (300 MHz, $CDCl_3$): 4.2-4.45 (m, 60H), 5.7-5.85 (d, 3H), 6.0-6.2 (m, 3H), 6.3-6.45 (d, 3H).

Example 4

Tris(acryloyl polyethylene glycol) phosphate

Experiment was conducted same as in Example 1 except that 16.55 g of polyethylene glycol mono acrylate (HOA, n=13.2) prepared in Preparation Example 4, 1.73 g of triethylamine and 0.8 g of phosphorous oxytrichloride were reacted, thereby providing 6.4 g of tris(acryloyl polyethylene glycol) phosphate (POA, n=10.3) (yield 40%).

$^1$H-NMR (300 MHz, $CDCl_3$): 4.2-4.45 (m, 158H), 5.7-5.85 (d, 3H), 6.0-6.2 (m, 3H), 6.3-6.45 (d, 3H).

Experimental Example 1

Ionic Conductivity Test

1. Test of Ionic Conductivity Depending on Plasticizer Content

Ionic conductivity of the electrolyte was measured of the electrolyte with varied contents of a plasticizer in the polymer electrolyte composition. Phosphate-based acrylate (POA, n=3) was used as a crosslinking agent. $LiCF_3SO_3$, $LiPF_6$ were used as lithium salt. Poly(ethylene glycol) dimethyl ether (n=4) and benzoyl peroxide (BPO) were used as a plasticizer and an initiator, respectively.

The composition was injected into a band-shaped conductive glass plate or a lithium-copper foil and thermally crosslinked. AC impedance between the band- or sandwich-shaped electrodes was measured under argon circumstance, and analyzed with a frequency response analyzer, thus obtaining complex impedance. A band-shaped electrode was prepared by applying a masking tape (1 mm×2 cm) on the center of conductive glass (ITO), followed by etching, washing and drying. Ionic conductivities with varied contents of the plasticizer were measured and the results are presented in Table 1.

TABLE 1

| Crosslinking Agent (g) | | Plasticizer PEGDMe, n = 4 (g) | Lithium salt $LiCF_3SO_3$(g) | Initiator BPO (g) | Ionic conductivity (S/cm, $\sigma \times 10^{-4}$) |
|---|---|---|---|---|---|
| POA | 0.3 | 0.7 | 0.12 | 0.009 | 3.68 |
| (n = 1) | 0.2 | 0.8 | 0.15 | 0.006 | 5.54 |
| | 0.1 | 0.9 | 0.17 | 0.003 | 6.75 |
| POA | 0.3 | 0.7 | 0.12 | 0.009 | 3.82 |
| (n = 3) | 0.2 | 0.8 | 0.15 | 0.006 | 5.90 |
| | 0.1 | 0.9 | 0.17 | 0.003 | 7.11 |
| POA (n = 5) | 0.1 | 0.9 | 0.17 | 0.003 | 7.57 |
| POA (n = 13.2) | 0.1 | 0.9 | 0.17 | 0.003 | 7.74 |

As shown in Table 1, ionic conductivity of a polymer electrolyte increases as the content of the plasticizer increases. It also increases along with the increase in the chain length of ethylene oxide of the crosslinking agent.

2. Ionic Conductivity Depending on the Kind of a Plasticizer and a Crosslinking Agent Phosphate-based acrylate (POA, n=1~13.2), $LiCF_3SO_3$ and BPO were also used as a crosslinking agent, a lithium salt, and an initiator, respectively. PEGDMe (n=4, 6, 7) and a mixed solvent of comprising propylene carbonate (PC) and ethylene carbonate (EC) in a mixing ratio of 1:1 were used as a plasticizer, and the ionic conductivity of electrolyte thin films prepared thereof was measured. The results are presented in Tables 2. The dependence of ionic conductivity with the various plasticizers is presented in FIG. 1.

As presented in Table 2 and FIG. 1, all the plasticizers showed similar behaviors. In particular, EC/PC plasticizer (polar aprotic solvent) causes superior ionic conductivity. Further, ionic conductivity increased with the increase in the chain length of the ethylene oxide of a crosslinking agent.

Experimental Example 2

Electrochemical Stability

A thin film for solid polymer electrolyte was prepared as described above on a nickel electrode (1 cm×1 cm) by using phosphate-based acrylate (POA, n=3) as a crosslinking agent and incorporating PEGDMe or EC/PC (1M $LiPF_6$) in the amount of 80 wt % as a plasticizer. A cell was prepared for measuring electrochemical stability by placing the electrolyte between lithium plates, and then packed under vacuum. Electrochemical stability was measured according to the LSV (linear sweep voltammetry) method in the potential range of −0.3-5.5 V at the sweep raste of 10 mV/sec, and the results are presented in FIG. 2.

As shown in FIG. 2, reversible oxidation/reduction of lithium was observed in the potential range of from −0.5 to 0.2 V. When PEGDME was used as a plasticizer, the current of electrolyte decomposition was not observed at a voltage of 5 V or less. These results show that a polymer electrolyte herein is electrochemically stable in a lithium standard electrode at a voltage of up to 5 V, thus being applicable to polymer electrolyte of lithium-polymer battery.

INDUSTRIAL APPLICABILITY

As described above, the present invention discloses a phosphate-based acrylate compound where a polyalkylene oxide group and a crosslinkable acrylate group are introduced to a phosphate-based compound. A phosphate-based acrylate compound herein is superior in mechanical strength, fire-retardancy and thermal and electrochemical stability, and thus can be applied to various fields. In particular, a solid polymer electrolyte composition, which comprises a phosphate-based acrylate compound herein as a crosslinking agent, includes a polyalkylene oxide group, thereby improving the compatibility with a plasticizer used for increasing the

TABLE 2

| Crosslinking agent (g) | | Plasticizer (g) | | Lithium salt $LiCF_3SO_3$ (g) | Initiator BPO (g) | Ionic conductivity (S/cm, $\square \times 10^{-4}$) |
|---|---|---|---|---|---|---|
| POA | 0.2 | PEGDMe, n = 4 | 0.8 | 0.15 | 0.006 | 5.54 |
| (n = 1) | 0.1 | | 0.9 | 0.17 | 0.003 | 6.75 |
| | 0.2 | PEGDMe, n = 6 | 0.8 | 0.16 | 0.006 | 4.08 |
| | 0.1 | | 0.9 | 0.18 | 0.003 | 5.83 |
| | 0.2 | PEGDMe, n = 7 | 0.8 | 0.17 | 0.006 | 2.68 |
| | 0.1 | | 0.9 | 0.19 | 0.003 | 3.81 |
| | 0.2 | EC/PC = 1:1 | 0.8 | — | 0.006 | 52 |
| | 0.1 | 1M $LiPF_6$ | 0.9 | — | 0.003 | 68 |
| POA | 0.2 | PEGDMe, n = 4 | 0.8 | 0.15 | 0.006 | 6.2 |
| (n = 3) | 0.2 | PEGDMe, n = 6 | 0.8 | 0.16 | 0.006 | 4.5 |
| | 0.2 | EC/PC = 1:1 1M $LiPF_6$ | 0.8 | 0.8 | 0.006 | 53 |
| POA | 0.2 | PEGDMe, n = 4 | 0.8 | 0.15 | 0.006 | 7.0 |
| (n = 5) | 0.2 | PEGDMe, n = 6 | 0.8 | 0.16 | 0.006 | 5.0 |
| | 0.2 | EC/PC = 1:1 1M $LiPF_6$ | 0.8 | — | 0.006 | 55 |
| POA | 0.2 | PEGDMe, n = 4 | 0.8 | 0.15 | 0.006 | 7.1 |
| (n = 13.2) | 0.2 | PEGDMe, n = 6 | 0.8 | 0.16 | 0.006 | 5.0 |
| | 0.2 | EC/PC = 1:1 1M $LiPF_6$ | 0.8 | — | 0.006 | 54 | ionic conductivity of an electrolyte. An acrylate group allows the formation of 3D network structure of a polymer electrolyte. This may be used to prepare an electrolyte thin film, and may be used for a polymer electrolyte of large capacity lithium-polymer secondary battery that can be applied for power storage device for load leveling or electric vehicles as well as a small capacity lithium-polymer secondary battery that can be applied to portable information terminals such as a mobile phone, a laptop computer.

The invention claimed is:

1. A solid polymer electrolyte composition comprising:
0.1-95 wt % of a phosphate-based acrylate crosslinking agent of Formula 1;
0.1-98 wt % of one or more of a plasticizer selected from polyalkylene glycol dialkyl ether of Formula 2 and a polar aprotic solvent;
3-40 wt % of a lithium salt; and
0.1-5 wt % of an initiator:

[Formula 1]

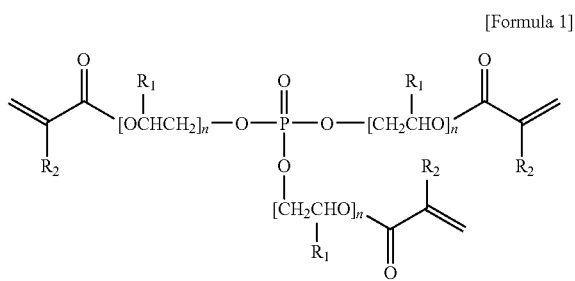

wherein $R_1$ and $R_2$ are respectively a hydrogen atom or a methyl group; and n is an integer of 1-20;

[Formula 2]

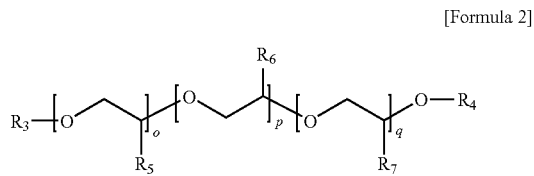

wherein $R_3$ and $R_4$ are respectively a $C_1$-$C_{10}$ a linear or branched alkyl group; $R_5$, $R_6$ and $R_7$ are respectively a hydrogen atom or a methyl group; o, p and q are respectively an integer of 0-20 except when all of o, p and q are zero at the same time.

2. The solid polymer electrolyte composition of claim 1, wherein the polar aprotic solvent is selected from the group consisting of alkylene carbonate-based, alkyltetrahydrofuran-based, dioxirane-based, lactone-based and acetonitrile-based solvents.

3. A thin film for solid polymer electrolyte, which is coated with the solid polymer electrolyte composition of claim 2.

4. A polymer electrolyte for lithium-polymer secondary battery, which comprises the solid polymer electrolyte composition of claim 2.

5. A lithium-polymer secondary battery, which comprises the solid polymer electrolyte composition of claim 2.

6. The solid polymer electrolyte composition of claim 1, wherein the lithium salt is selected from the group consisting of $LiClO_4$, $LiCF_3SO_3$, $LiBF_4$, $LiPF_6$, $LiAsF_6$ and $Li(CF_3SO_2)_2N$.

7. A thin film for solid polymer electrolyte, which is coated with the solid polymer electrolyte composition of claim 6.

8. A polymer electrolyte for lithium-polymer secondary battery, which comprises the solid polymer electrolyte composition of claim 6.

9. A lithium-polymer secondary battery, which comprises the solid polymer electrolyte composition of claim 6.

10. A thin film for solid polymer electrolyte, which is coated with the solid polymer electrolyte composition of claim 1.

11. A polymer electrolyte for lithium-polymer secondary battery, which comprises the solid polymer electrolyte composition of claim 1.

12. A lithium-polymer secondary battery, which comprises the solid polymer electrolyte composition of claim 1.

* * * * *